United States Patent
Kanamaru (10) Patent No.: US 7,753,919 B2
(45) Date of Patent: Jul. 13, 2010

(54) WIRE FOR REMOVING INTRAVASCULAR FOREIGN BODY AND MEDICAL INSTRUMENT

(75) Inventor: Takeshi Kanamaru, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 11/219,876

(22) Filed: Sep. 7, 2005

(65) Prior Publication Data

US 2006/0052797 A1 Mar. 9, 2006

(30) Foreign Application Priority Data

Sep. 7, 2004 (JP) ............... 2004-260098

(51) Int. Cl.
*A61B 17/24* (2006.01)
*A61B 17/26* (2006.01)
*A61M 29/00* (2006.01)

(52) U.S. Cl. ..................... 606/114; 606/200

(58) Field of Classification Search ......... 606/200, 606/113–114, 127, 106, 108, 110, 128, 159, 606/191, 194, 198; 623/1.1
See application file for complete search history.

(56) References Cited

U.S. PATENT DOCUMENTS

| | | | | |
|---|---|---|---|---|
| 4,347,846 A | * | 9/1982 | Dormia ............. | 606/127 |
| 5,562,678 A | * | 10/1996 | Booker ............. | 606/113 |
| 5,906,622 A | * | 5/1999 | Lippitt et al. ........ | 606/127 |
| 5,993,474 A | * | 11/1999 | Ouchi ............. | 606/206 |
| 6,174,318 B1 | * | 1/2001 | Bates et al. .......... | 606/127 |
| 6,416,519 B1 | | 7/2002 | VanDusseldorp | |
| 2002/0019640 A1 | | 2/2002 | McGuckin, Jr. | |
| 2002/0072764 A1 | | 6/2002 | Sepetka et al. | |
| 2003/0018355 A1 | | 1/2003 | Goto et al. | |
| 2003/0135233 A1 | * | 7/2003 | Bates et al. .......... | 606/200 |
| 2003/0225419 A1 | * | 12/2003 | Lippitt et al. ........ | 606/127 |
| 2004/0167567 A1 | | 8/2004 | Cano et al. | |

FOREIGN PATENT DOCUMENTS

JP 2004-016668 1/2004

OTHER PUBLICATIONS

European Search Report for EP 05 01 8587, dated Dec. 15, 2005.

* cited by examiner

*Primary Examiner*—Todd E Manahan
*Assistant Examiner*—Lindsey Bachman
(74) *Attorney, Agent, or Firm*—Buchanan Ingersoll & Rooney PC (57) ABSTRACT

A wire for removing an intravascular foreign body comprises a flexible wire body, a branch part branching out from the forward end of the wire body, and a plurality of filaments extending across the branch part. The branch part and the filaments form a space for capturing a foreign body therein. At least one of the filaments is changeable in length so that the loop formed by the filament and the branch part changes in size. The wire is capable of relatively reliably capturing and removing a foreign body in the vessel.

31 Claims, 10 Drawing Sheets

DETAILED DESCRIPTION

Figure 1:
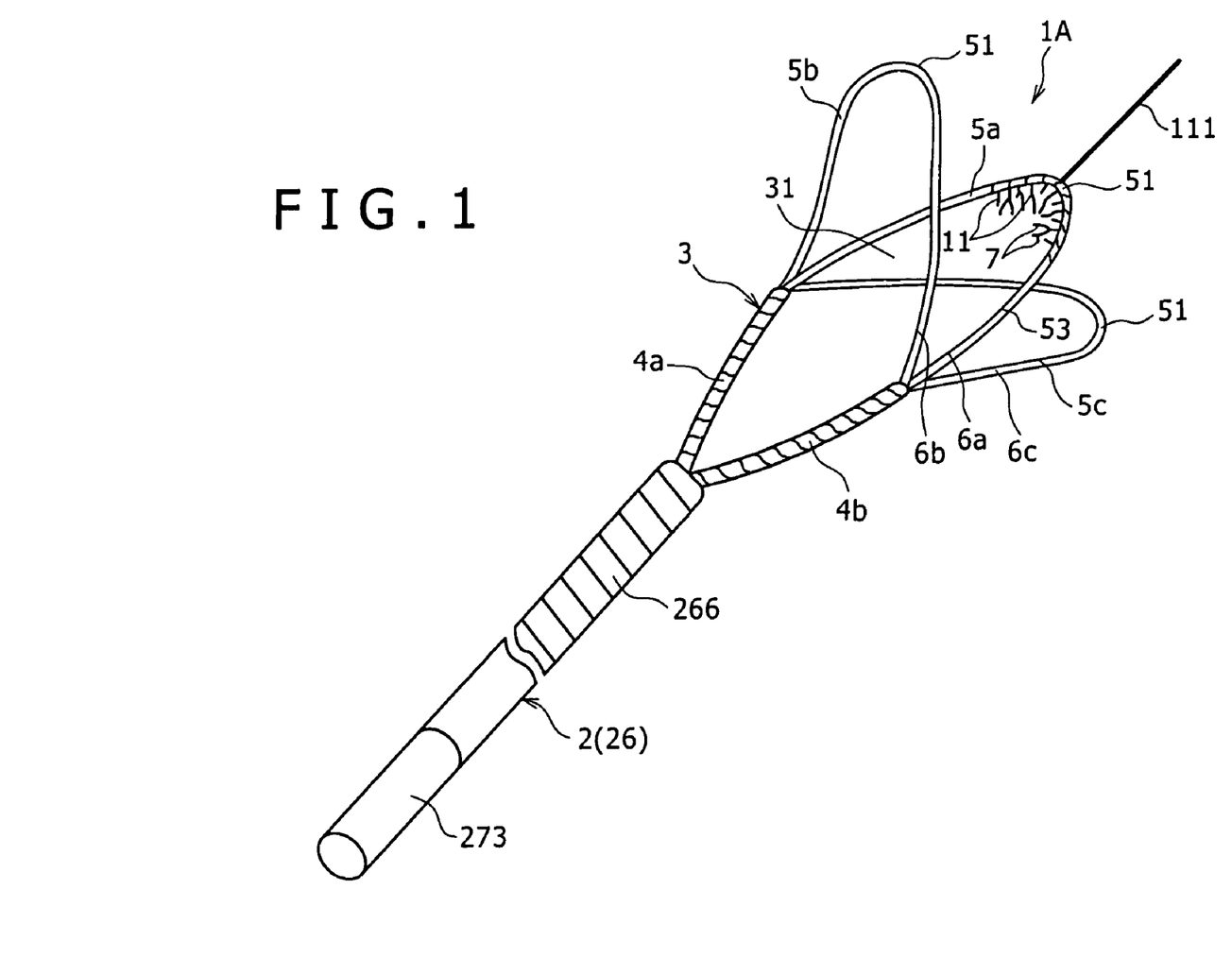
Figure 2:
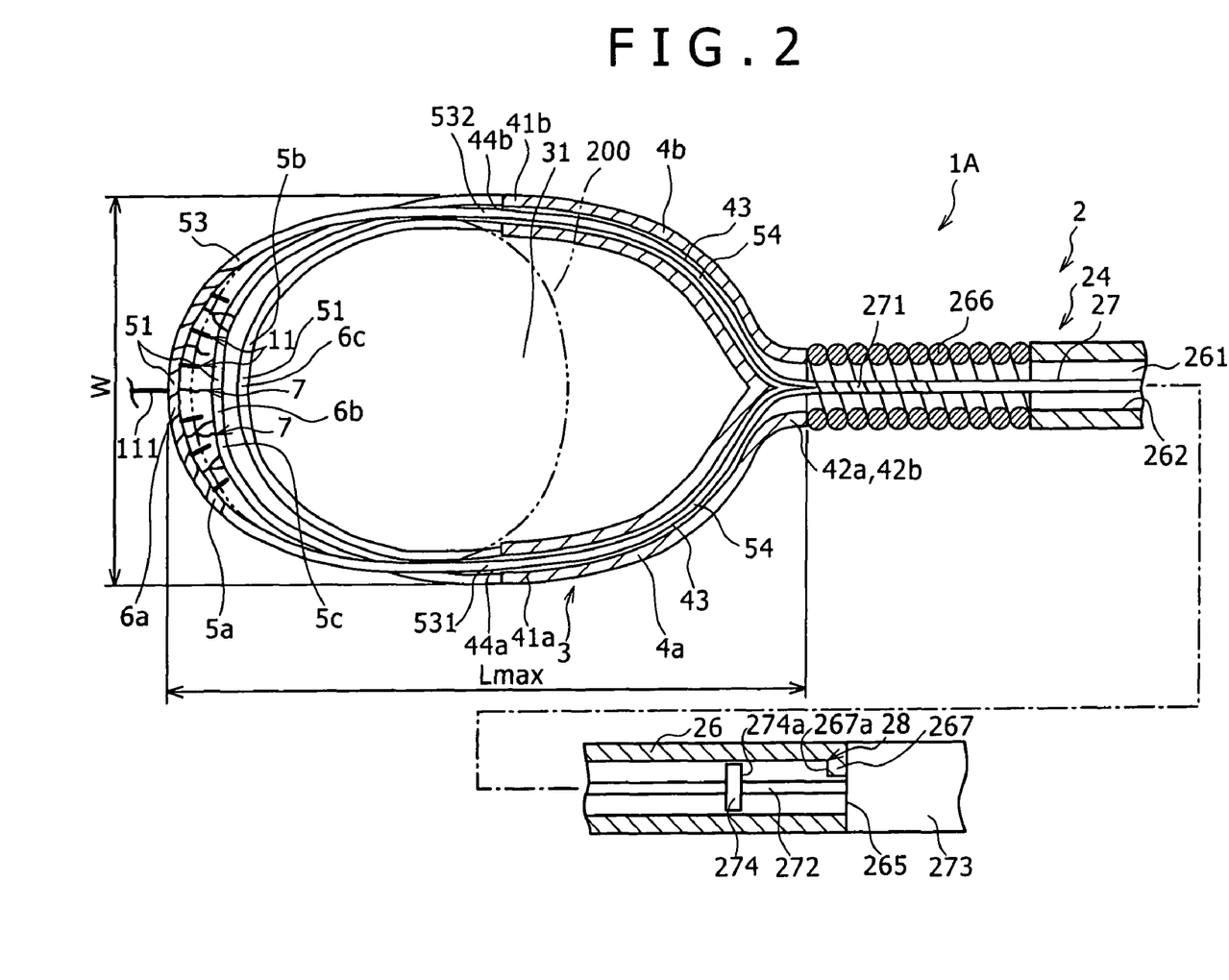
Figure 3:
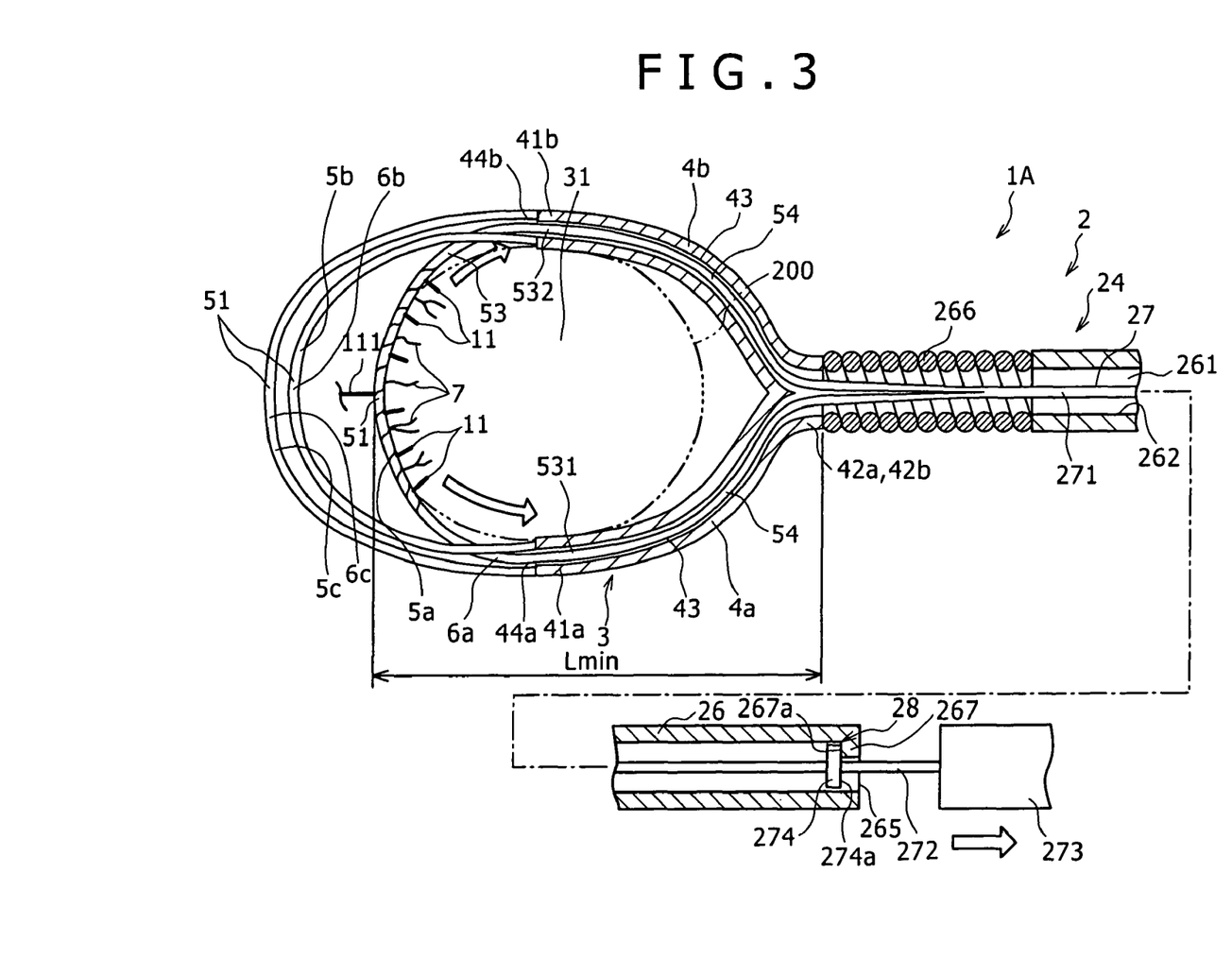
Figure 4:
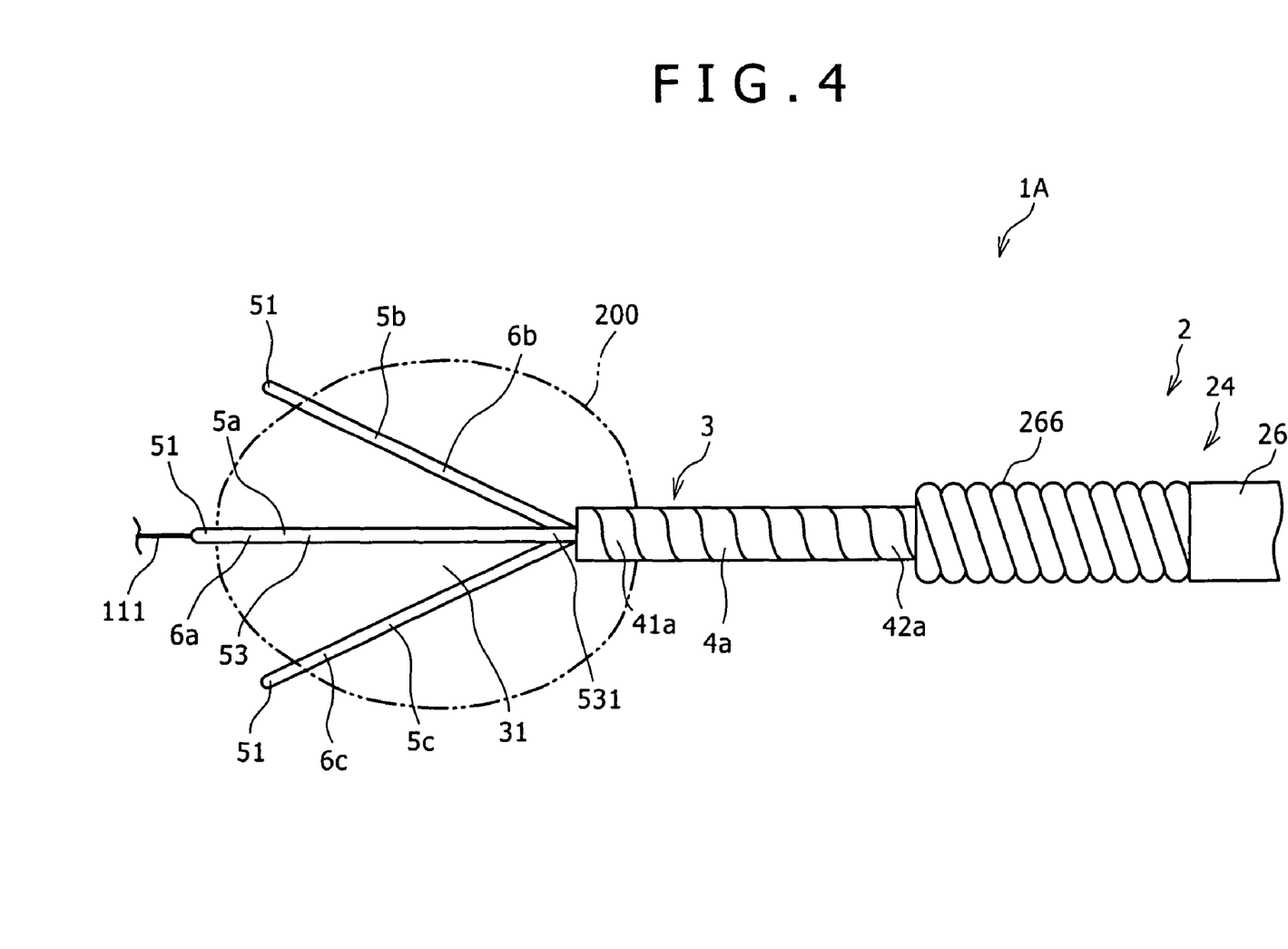

FIG. 1 is a perspective view of one embodiment of a wire for removing an intravascular foreign body, FIGS. 2 and 3 are plan views, partially in longitudinal cross-section, of the wire for removing an intravascular foreign body shown in FIG. 1, FIG. 4 is a side view of the wire for removing an intravascular foreign body shown in FIG. 1, and FIGS. 5-9 are general or somewhat schematic illustrations showing a manner of use associated with the wire for removing an intravascular foreign body shown in FIG. 1.

The terms "base end" and "forward end" in the following description are defined as follows. In FIG. 1, the upper right side is the "forward end (distal end)" and the lower left side is the "base end (proximal end)", while in FIGS. 2-9, the left side is the "forward end (distal end)" and the right side is the "base end (proximal end)".

Referring to FIG. 1, a wire 1A for removing an intravascular foreign body is adapted to capture and remove a foreign body, such as a thrombus and/or a clot, which can cause an embolism in vessel (blood vessel). The following description refers to an embolus 200 as an example of the intravascular foreign body A.

The wire 1A for removing an intravascular foreign body comprises a long or elongated wire body 2 and a capturing part 3 attached to the forward end of the wire body 2. The capturing part 3 is constructed to capture the embolus 200 in the vessel 100.

Referring to FIG. 2, the wire body 2 includes a tube 26 and a linear body 27 which passes through the inside 261 of the tube 26. The wire body 2 has adequate rigidity and resilience (flexibility) over its entire length.

The tube 26 comprises a coil 266 arranged at the forward end portion of the tube and connected to the forward end portion of the tube 26. The coil 266 makes the forward end of the tube 26 more resilient (or flexible).

As shown in FIGS. 2 and 3, the linear body 27 is constructed such that it can move relative to the tube 26. The linear body 27 includes a base 272 and is constructed such that the base 272 can project beyond the base-end opening 265 of the tube 26 as generally shown in FIG. 3.

The linear body 27 also includes a manipulating member 273 attached to the base end 272 of the linear body 27. The manipulating member 273 is designed to manipulate or move the linear body 27 in its lengthwise direction. The manipulating member 273 can be grasped by the user and facilitates the operation of the linear body 27.

The parts constructing the wire body 2 may be formed from any materials without specific restrictions, such as metallic and plastic materials, which may be used alone or in combination.

The length of the wire body 2 may vary depending on the position and size of the vessel 100 to which it is applied. A preferred length ranges from 500 to 4000 mm, more preferably 1500 to 2200 mm.

The wire body 2 (or the tube 26) may also vary in thickness (outside diameter) depending on the position and size of the vessel 100 to which it is applied. A preferred outside diameter is 0.1 to 2.0 mm on average, more preferably 0.25 to 0.9 mm.

If the wire 1A for removing an intravascular foreign body is to be inserted into a microcatheter, the outside diameter of the wire body 2 should preferably be 0.1 to 0.53 mm (0.004 to 0.021 inches), more preferably 0.25 to 0.46 mm (0.010 to 0.018 inches).

The reference to a microcatheter refers to a catheter for intravascular treatment and/or diagnosis which has an outside diameter no larger than 4 French (equal to approximately 1.33 mm). Microcatheters are clearly distinguished from angiography catheters and guiding catheters having an outside diameter equal to or larger than 4 French.

The wire body 2 (or the tube 26) should preferably be composed of a first part (which is comparatively hard and is located at the base end), a third part (which is comparatively soft and is located at the forward end), and a second part (which is variable in flexibility and is located at the intermediate position between the first part and the third part). In other words, the wire body 2 should preferably be formed in such a way that it gradually decreases in rigidity (flexural and torsional rigidity) from its base end to its forward end. The gradually changing rigidity permits the manual manipulation to be reliably transmitted to the forward end 24 (including the coil 266) of the wire body 2. With such properties making the forward end 24 relatively flexible, the wire body 2 is able to proceed and bend in the vessel 100 without damaging the vessel 100. Such properties permit the wire body 2 to transmit its twisting motion and its pushing motion while inhibiting or preventing kinking (or flexing). This contributes to higher safety.

The wire body 2 (or the tube 26) may have a coating layer on its outer surface to reduce friction with the inside of the catheter 8 (described later). The coating layer permits relatively smooth insertion into and removal from the catheter. The coating layer may be formed from a fluorocarbon resin (such as polytetrafluoroethylene or Teflon®) or a hydrophilic polymer which becomes lubricious in a wet condition.

The linear body 27 may also have a coating layer on its outer surface (as in the case of the tube 26) for reducing friction with the internal surface 262 of the tube 26. The coating layer produces the same effect as mentioned above.

The capturing part 3 is located at the forward end of the wire body 2. FIGS. 2 and 3 illustrate the capturing part 3 as being open in its natural state. "Open" means that the width expands in the vertical direction in FIGS. 2 and 3. This state is referred to as the "expanded state" hereinafter. In its expanded state, a space is formed in the capturing part 3 for capturing a foreign body or embolus 200 in the vessel 100.

The capturing part 3 is changeable in shape or collapsible. In other words the capturing part is capable of collapsing to become smaller in size so that it is able to be received or held in the catheter 8. This state is referred to as the "collapsed state" hereinafter. The capturing part 3 is capable of changing from its collapsed state to its expanded state by its own elasticity.

In the following description, it is assumed that the shape and size of the capturing part 3 is such that the capturing part 3 is in its expanded state (or natural state), unless otherwise mentioned.

As shown in FIG. 1, the capturing part 3 comprises two branch wires (branch part) 4a, 4b and three filaments 5a, 5b, 5c. The two branch wires branch from the forward end of the coil 266 (or the forward end of the wire body 2) and extend apart from one another (i.e., diverge in a direction away from the wire body 2). The three filaments extend from the one branch wire 4a to the other branch wire 4b.

The branch wires 4a, 4b are constructed as hollow wires. The hollow wires can include not only pipe-like or tubular wires, but also coils and braided wires with a hollow interior. The illustrated example is constructed as follows. The coil 266 is composed of at least four fine wires. These four wires are separated into two wires at the forward end of the coil 266, and these two wires are twisted to make the hollow twisted wires forming the branch wires 4a, 4b. It is also possible to form the branch wires 4a, 4b by fixing a branched pipe-like member to the forward end of the coil 266.

The base ends 42a, 42b of the respective branch wires 4a, 4b (loop wires 6a, 6b, 6c) are fixed to the forward end of the coil 266 so that the hollow part 43 of each branch wire 4a, 4b communicates with the bore 261 of the tube 26.

The above description described one way of connecting the branch wires 4a, 4b to the coil, but it is to be understood that no specific restrictions are imposed on the method of fixing the branch wires 4a, 4b to the coil 266. One method may involve winding the base ends 42a, 42b of the branch wires 4a 4b around the forward end of the coil 266 and then performing brazing, welding, or adhesion with an adhesive.

The three filaments 5a, 5b, 5c extend from the forward end 41a of the branch wire 4a to the forward end 41b of the branch wire 4b. As shown in FIG. 2, the filament 5a has connecting parts 54 which connect a space forming part 53 of the filament 5a (which forms the space 31 in which is captured the foreign body) to the linear body 27 of the wire body 2.

The space forming part 53 projects forward from the forward openings 44a, 44b of the branch wires 4a, 4b. The space forming part 53 assumes an arch-like shape which curves in the illustrated manner.

The connecting parts 54 are formed at the respective ends 531, 532 of the space forming part 53. The connecting parts 54 pass through the respective bore 43 of the branch wires 4a, 4b and are fixed to the forward end 271 of the linear body 27. No specific restriction is imposed on the method of fixing. For example, the fixing methods mentioned above for the branch wires 4a, 4b may be used.

The connecting parts 54 permit the space forming part 53 to be introduced relatively easily into the hollow part 43 of the branch wires 4a and 4b.

As shown in FIG. 4, the filament 5a constructed as mentioned above is positioned approximately on the plane (perpendicular to the paper in FIG. 4) passing through the extension line of the central axis of the wire body 2. In other words, the filament 5a overlaps approximately with the extension line of the central axis of the wire body 2 in the side view (FIG. 4) so that the central axis and the filament 5a lie in a common plane.

As shown in FIG. 2, the filaments 5b, 5c curve in such a way that their apexes 51 bulge toward the forward end, and they connect the forward end 41a of the branch wire 4a to the forward end 41b of the branch wire 4b.

Also, the filaments 5b, 5c are inclined such that the distance from each filament to the extension line of the central axis of the wire body 2 increases in the direction toward the forward end. In other words, in the side view of FIG. 4, the filament 5b is inclined left-upward and the filament 5c is inclined left-downward.

The filaments 5b, 5c fixed and arranged in this manner advantageously produce the effect that when the capturing part 3 captures the embolus 200, they keep the captured embolus 200 from being carried by blood flow.

The capturing part 3 has the capturing space 31 (for capturing or trapping the embolus 200 therein) which is surrounded by the branch wires 4a, 4b and the filaments 5a, 5b, 5c. In other words, the filaments 5a, 5b, 5c form a basket-like part for holding the foreign body.

With the construction of the wire 1A for removing an intravascular foreign body described above, the wire 1A can be said to comprise three loop wires 6a, 6b, 6c extending from the forward end of the wire body 2. In this illustrated embodiment, the loop wires are comprised of the branch wires 4a, 4b and the filaments 5a, 5b, 5c. Each of the loop wires 6a, 6b, 6c extends forwardly from the forward end of the wire body 2 and returns to the forward end of the wire body 2 after forming a loop.

As briefly described above, the wire 1A for removing an intravascular foreign body also comprises the manipulating member 273 which can be moved in the base end direction (to the right in FIG. 3). In this way, it is possible to change the size of the loop wire 6a. Thus, the loop wire 6a can vary in size from a maximum or first state shown in FIG. 2 to a minimum or second state shown in FIG. 3.

The loop wire 6a can be moved or shifted from the first state to the second state in the following manner. First, the manipulating member 273 is pulled in the base end direction (i.e., in the direction of the arrow in FIG. 3 away from the end of the tube 26) so that the ends 531, 532 of the space forming part 53 are pulled or moved into the hollow part 43 of the branch wires 4a, 4b. As a result, the projecting length of the space forming part 53 changes and becomes shorter. That is, the loop wire 6a changes from the first state into the second state so that the space becomes smaller as illustrated by comparing FIGS. 2 and 3.

The embolus 200 which has been captured in the foreign body capturing space 31 when the loop wire 6a is in the first state is thus tightened and held by the loop wire 6a as the loop wire 6a is shifted to the second state. In this way it is possible to prevent the captured embolus 200 from slipping out from the foreign body capturing space 31 and hence it is possible to relatively reliably capture the embolus 200 and eventually remove the embolus 200 from the vessel 100.

In the wire 1A for removing an intravascular foreign body as descried above, the length or size of the space forming part is changed through utilization of one filament. This construction may be modified such that the space forming part changes in length or size through utilization of two or more filaments.

While it is desirable to form a coating layer (like the one explained above for the tube 26 of the wire body 2) on the outer surface of the connecting parts 54 of the filament 5a and the linear body 27 of the wire body 2, it is also desirable to form a coating layer (like the one explained above for the tube 26 of the wire body 2) on the inner surface of the branch wires 4a, 4b and the inner surface (internal peripheral surface 262) of the tube 26 of the wire body 2.

As shown in FIG. 3, a control means 28 is provided to control the size of the loop wire 6a in the second state. This size controlled by the control means 28 is referred to as the "minimum loop diameter" hereinafter.

The control means 28 comprises a projecting part 267 and an expanded part 274. The projecting part 267 projects generally in the radial direction from the inside 262 of the tube 26 in the neighborhood of the base opening 265 of the tube 26. The expanded part 274 is a part which expands generally in the radial direction from the outside of the linear body 27 in the bore 261 of the tube 26. The expanded part 274 can be formed by fixing a ring-shaped member to the linear body 27.

The projecting part 267 of the tube 26 and the expanded part 274 of the linear body 27 are constructed such that the face 267a at the forward end side of the projecting part 267 comes into contact with the face 274a at the base end side of the expanded part 274 when the loop wire 6a assumes the second state or when the linear body 27 is moved towards the base end direction relative to the tube 26. This prevents the linear body 27 from moving excessively toward the base end.

The control means 28 constructed as mentioned above protects the embolus 200 from being excessively tightened or squeezed by the loop wire 6a. In this way it is possible to prevent the embolus 200 from being broken by the loop wire 6a.

The size of the minimum loop diameter (the length indicated by Lmin in FIG. 3) is not specifically restricted so long as it is smaller than Lmax. If Lmax is 8 to 15 mm, Lmin should preferably be 1 to 7.5 mm, preferably 3 to 5 mm.

The expanded part 274 can be constructed so that its position relative to the linear body 27 is adjustable. In this way, the minimum loop diameter can be varied by adjusting the position of the expanding part 274. It is thus possible to establish the minimum loop diameter according to the size of the embolus 200.

The outside diameters of the branch wire 4a, 4b are not specifically restricted. The diameters should preferably be 0.05 to 0.9 mm, more preferably 0.1 to 0.5 mm. Also, the outside diameters of the filaments 5a, 5b, 5c are not specifically restricted. The outside diameters of the filaments 5a, 5b, 5c should preferably be 0.025 to 0.2 mm, more preferably 0.05 to 0.1 mm.

The size of the capturing part 3 may be established as desired and can vary depending on the vessel thickness and the case or type of disease. The overall length indicated by Lmax in FIG. 2 is usually 2 to 40 mm, preferably 4 to 20 mm. The outside diameter or width (indicated by W in FIG. 2) of the capturing part 3 in its expanded state should preferably be 1 to 30 mm, more preferably 2 to 5 mm.

For use in the cerebral artery end (M1 portion), the capturing part 3 should have an overall length (indicated by Lmax in FIG. 2) of at least 7 mm, preferably 8 to 15 mm, and an outside diameter (indicated by W in FIG. 2) of 2 to 5 mm, in its expanded state. This is because the inside diameter of the vessel in the cerebral artery end (M1 portion), where brain infarction occurs frequently, is about 3 to 4 mm and, according to doctors' experience, the size of thrombus causing embolus is about 3 mm in outside diameter and about 7 mm in length in many cases.

As mentioned above, the capturing part 3 is capable of deforming or changing into the collapsed state so that it can pass through (or can be inserted into) the lumen 82 of a catheter 8. According to the present invention, the capturing part 3 is comparatively simple in structure so that it can be made thin easily in its collapsed state.

According to the above-described embodiment, the capturing part 3 is able to returns to its expanded state from its collapsed state by its own resilience, owing to the comparatively highly rigid (comparatively thick) branch wires 4a, 4b. Moreover, the comparatively flexible (comparatively thin) filaments 5a, 5b, 5c reliably hold the embolus 200 while preventing it from slipping out of the capturing space. Thus the capturing part 3 can be relatively small in diameter (in its collapsed state) when it captures the embolus 200.

The capturing part 3 can be as small in diameter as an ordinary guide wire and so the wire 1A for removing an intravascular foreign body can be used in combination with existing microcatheter.

The ratio of W/W' (where W is the outside diameter or width mentioned above of the capturing part 3 in its expanded state and W' is the outside diameter or width of the capturing part 3 in its collapsed state) should preferably be about 1.1 to 20, more preferably 1.1 to 10.

When used in combination with a microcatheter, the outside diameter W' in the collapsed state should be smaller than 0.53 mm (0.021 inches), more preferably smaller than 0.46 mm (0.018 inches).

The capturing part 3 returns from its collapsed state to its expanded state by its own elasticity as the wire 1A for removing an intravascular foreign body (the wire body 2) is advanced relative to the catheter 8 so that the capturing part 3 is pushed out (exposed) from the forward opening 81 of the catheter 8.

As the wire 1A for removing an intravascular foreign body is retreated toward the base end of the catheter 8 (i.e., pulled into the catheter after being advanced), the base ends of the branch wires 4a, 4b come into contact with the edge of the forward opening 81 and then enter the catheter 8. Thus the distance between the branch wires 4a, 4b decreases.

As the wire 1A for removing an intravascular foreign body is retreated further toward the base end of the catheter, the capturing part 3 assumes the collapsed state automatically, with the distance between the branch wires 4a, 4b being decreased, and the capturing part 3 is received (held) again in the catheter 8.

As mentioned above, the capturing part 3 deforms from its expanded state to its collapsed state automatically and vice versa as it enters or leaves the forward opening 81 of the catheter 8.

The capturing part 3 (loop wires 6a, 6b, 6c) should preferably be formed from any radiopaque material which is not specifically restricted. Materials include, for example, gold, platinum, platinum-iridium alloy, tungsten, tantalum, palladium, lead, silver, and their alloys and compounds. Such radiopaque materials facilitate manipulation to capture the embolus 200 by the capturing part 3 with the help of X-ray radioscopy and the like.

The capturing part 3 (loop wires 6a, 6b, 6c) may be formed from various metallic materials and plastic filaments (mono- or multi-). Metallic materials include stainless steel (such as SUS 304), β-titanium steel, Co—Cr alloy, piano wire, platinum-iridium alloy (Pt90-Ir10, Pt80-Ir20), noble metal alloy, nickel-titanium alloy, and other alloys having springy properties.

Of these metallic materials for the capturing part 3, the one which exhibits superelasticity in the living organism is preferable. Such material is able to reliably change from the collapsed state to the expanded state, and vice versa.

Alloys that exhibit superelasticity in the living organism refers to materials which are restored nearly to their original shape after deformation (bending, stretching, and compressing) to an extent at which ordinary metals undergo plastic deformation at the living body temperature (about 37° C.). Such materials also include so-called shape memory alloy and superelastic alloy.

The specific shape memory alloy and superelastic alloy are not specifically restricted. Titanium alloys (Ti—Ni, Ti—Pd, Ti—Nb—Sn) and copper alloys are preferable. The titanium alloys should preferably be composed of 30 to 52 atom % of titanium, with the remainder being nickel and one or more optional elements (equal to or less than 10 atom %). The optional elements, which are not specifically restricted, may be selected from iron, cobalt, platinum, palladium, and chromium (each equal to or less than 3 atom %), and copper and vanadium (each equal to or less than 10 atom %).

Preferred superelastic alloys are those which undergo transformation from austenite phase at normal temperature or body temperature (about 37° C.) into martensite phase under stress.

The surface of the capturing part 3 should be provided with means for preventing the embolus 200 (which has been captured) from slipping off from the capturing part 3. Such anti-slipping means increases friction between the capturing part 3 and the embolus 200, thereby allowing the capturing part 3 to reliably capture the embolus 200 and reliably hold the captured embolus 200.

The anti-slipping means is not specifically restricted. It may be formed by coating with an elastic material (such as rubber) having a comparatively high coefficient of friction or by sand blasting which produces fine rough surfaces or surface irregularities.

The outer surface of the capturing part 3 (filaments 5a, 5b, 5c) may be provided with a coating layer as explained above for the wire body 2. The coating layer permits the capturing part 3 to be inserted into and removed from the catheter 8 relatively easily.

The filament 5a and the linear body 27 of the wire body 2 may be constructed of separate materials or may be integrally formed with the same material.

As shown in FIG. 2, the filament 5a (the space forming part 53) has a plurality of projections 11 which project into the foreign body capturing space 31. The projections 11 may be formed in any manner which is not specifically restricted. One method may involve winding one end of a number of flexible linear bodies (wires) around the filament 5a, while allowing the other small end to project towards the capturing space 31.

Other ends of each linear body are gathered (or twisted together) in the vicinity of the apex 51 of the filament 5a so that they project into the forward end. Thus other ends of the linear bodies function as the guide wire 111.

Each of the projections 11 may be formed from any material, the specific type of which is not specifically restricted. Metallic materials or plastic materials may be used alone or in combination with one another.

The length (on average) of each projection is also not specifically restricted. The length should preferably be 0.1 to 5 mm, more preferably 0.5 to 2 mm.

As shown in FIG. 2, the filament 5a (the space forming part 53) also has a plurality of flexible fine fibers 7 projecting into the foreign body capturing space 31. Each fine fiber 7 should preferably be softer or more flexible than the projection 11.

Each of the fine fibers 7 may be formed in any manner which is not specifically restricted. For example, one method may involve winding a fibrous body (having fine fibers 7) around the filament 5a or attaching fine fibers to the filament 5b by static flocking.

The fine fibers 7 may be formed from any material, the specific type of which is not specifically restricted. The material includes radiation-transparent fibers such as Dacron (polyester), polyglycolic acid, polylactic acid, fluoropolymer (polytetrafluoroethylene), nylon (polyamide), cotton, and silk. Other materials include metallic yarn coated with radiation-transparent fiber or radiation-opaque fiber.

The length (on average) of each fine fiber 7 is also not specifically restricted. The fine fiber should preferably be 0.1 to 5 mm in length, more preferably 0.5 to 3 mm.

The projections 11 and the fine fibers 7 formed as mentioned above and directed into the capturing space 31 make it possible to relatively reliably capture the embolus 200. In the case of a comparatively hard embolus 200, the projections 11 stab the embolus 200, thereby inhibiting or preventing it from slipping out from the foreign body capturing space 31. In the case of a comparative soft embolus 200, the fine fibers 7 hang on to the embolus 200, thereby inhibiting or preventing it from slipping off from the foreign body capturing space 31.

The projections 11 directed into the capturing space 31 may be formed not only on the filament 5a but also on the filaments 5b, 5c or on any one of the filaments 5a, 5b, 5c. Also, the fine fibers 7 may be formed not only on the filament 5a but also on the filaments 5b, 5c or on any one of the filaments 5a, 5b, 5c.

A medical instrument 9 according to the present invention includes the wire 1A for removing an intravascular foreign body together with the catheter 8.

Set forth below is a description of one way of using the wire 1A for removing an intravascular foreign body.

Figure 5:
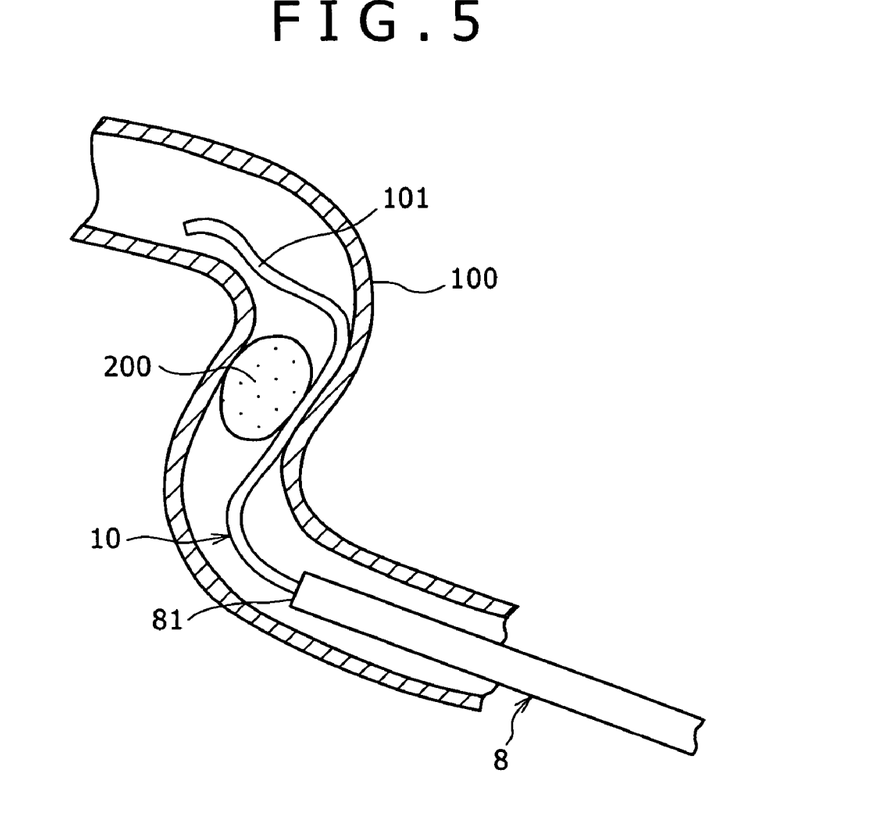

[1] FIG. 5 depicts a vessel 100 which is clogged with an embolus 200 (such as thrombus) which hinders blood flow. The embolus 200 is almost immobile because it is pushed against the inner wall of the vessel 100 by blood pressure.

The first step involves inserting the catheter (microcatheter) 8 and the guide wire 10 (which has been passed through the lumen 82 of the catheter 8) into the vessel 100. The second step is to project a forward end 101 of the guide wire 10 from the forward open end 81 of the catheter 8 beyond the embolus 200. In other words, the second step is carried out such that the forward end 101 of the guide wire 10 passes through the gap between the embolus 200 and the inner wall of the vessel 100 and moves beyond the embolus 200. This operation can be relatively easily accomplished by using the guide wire 10 (micro-guide wire) which has good lubricity.

Figure 6:
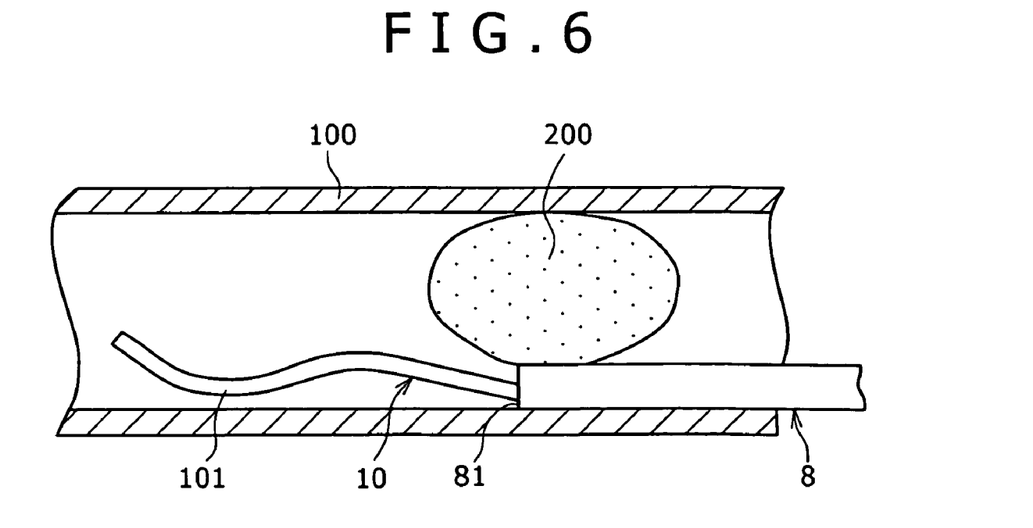

[2] After the forward end 101 of the guide wire 10 has moved past the embolus 200, the catheter 8 is advanced relative to the guide wire 10 so that the forward end of the catheter 8 moves into the gap between the embolus 200 and the inner wall of the vessel 100 as shown in FIG. 6. This operation can be relatively easily accomplished because the forward end of the catheter 8 smoothly moves along the guide wire 10 and into the gap.

According to the conventional therapy, the above-mentioned operations are followed by injecting a thrombolitic agent through the catheter 8. However, in doctors' experience, there are emboli 200 which are not dissolved by a thrombolitic agent or dissolution by a thrombolitic agent takes a long time. The present invention is effective in such a case.

Figure 7:
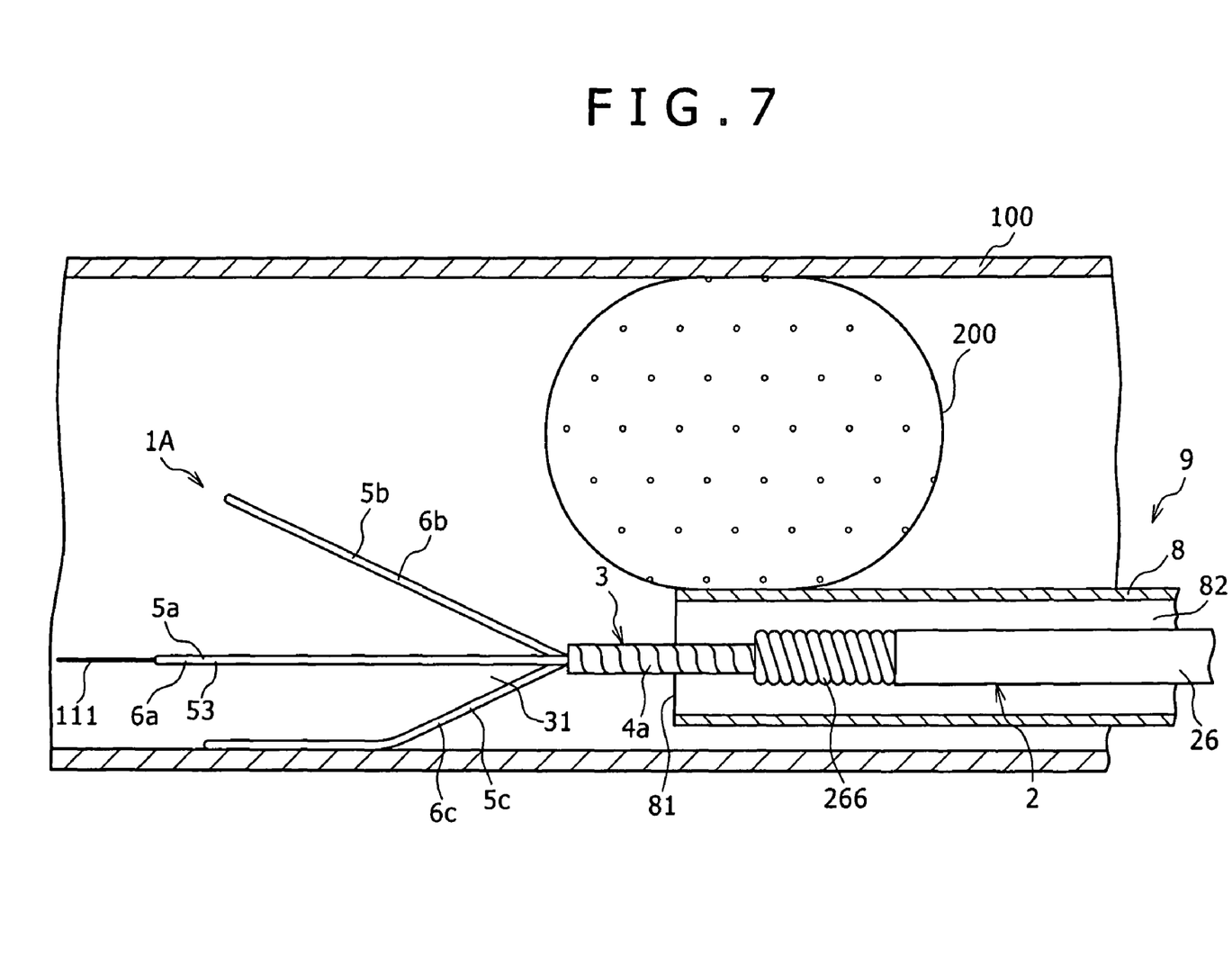

[3] The step shown in FIG. 6 is followed by the next step in which the guide wire 10 is removed and the wire 1A for removing an intravascular foreign body is inserted into the lumen 82 of the catheter 8. As shown in FIG. 7, the wire 1A for removing an intravascular foreign body is advanced so that the capturing part 3 projects from the forward opening 81 of the catheter 8 so that the capturing part 3 (which has been in its collapsed state) expands automatically by its own elasticity and is switched over to its expanded state. When the capturing part assumes its expanded state, the foreign body capturing space 31 that captures the embolus 200 is formed.

Figure 8:
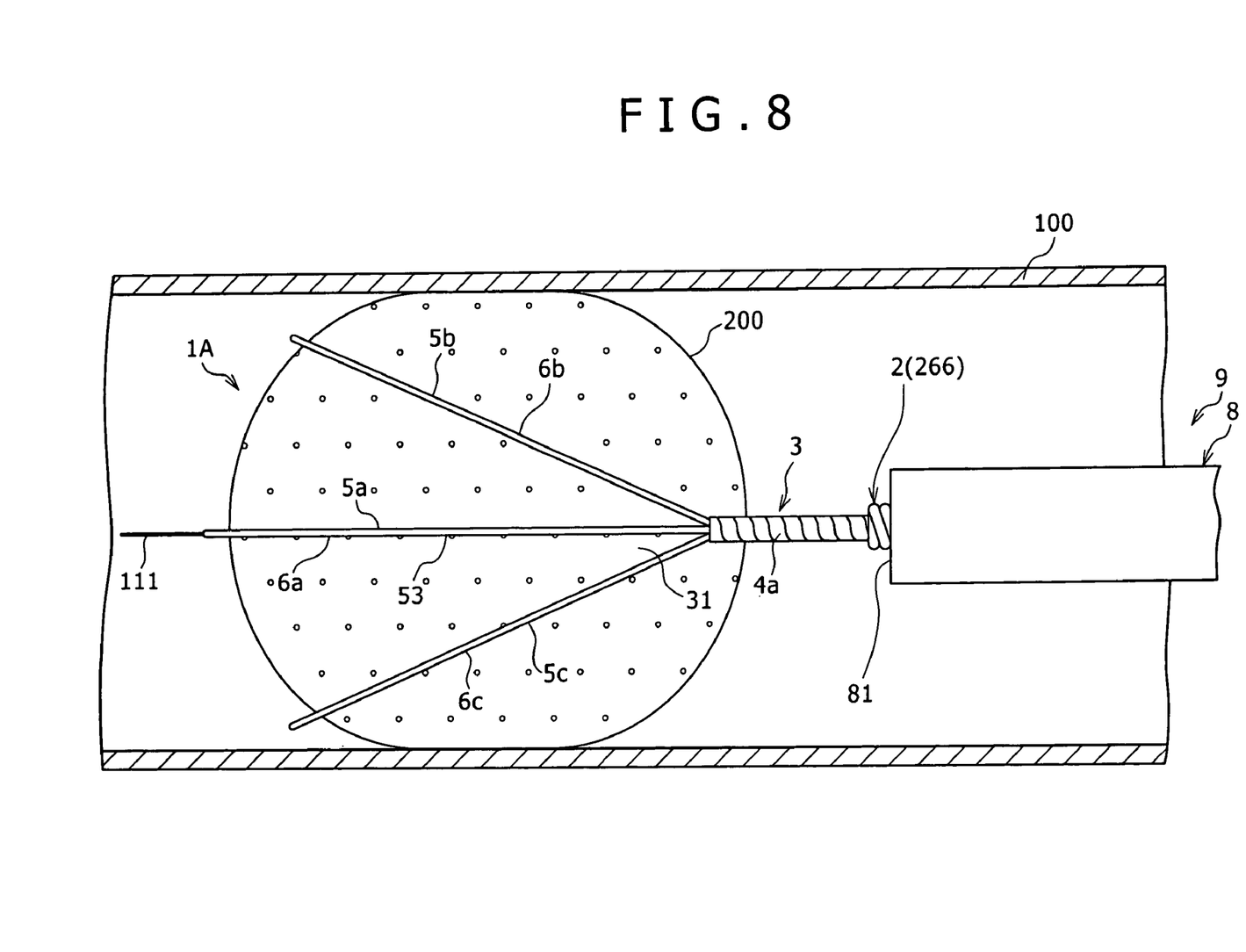
FIG. 8 is a general illustration of a manner of using the wire for removing an intravascular foreign body which is shown in FIG. 1.

[4] Then, the catheter 8 is slightly moved in the base end direction so that the forward end of the catheter 8 is retreated to the back end of the embolus 200. Now, the embolus 200 is captured (scooped) by the foreign body capturing space 31 of the capturing part 3 as shown in FIG. 8. In other words, the embolus 200 enters the foreign body capturing space 31 from the upper side shown in FIGS. 7 and 8.

[5] The loop wire 6a is then made small (i.e., the area enclosed by the loop wire 6a is reduced) by operating the manipulating member 273 of the linear body 27 so that the embolus 200 is drawn toward the branch wires 4a, 4b. The loop wire 6a is then made smaller (i.e., the area enclosed by the loop wire 6a is reduced) so that the embolus 200 is tightened by the loop wire 6a as shown in FIG. 9.

Figure 9:
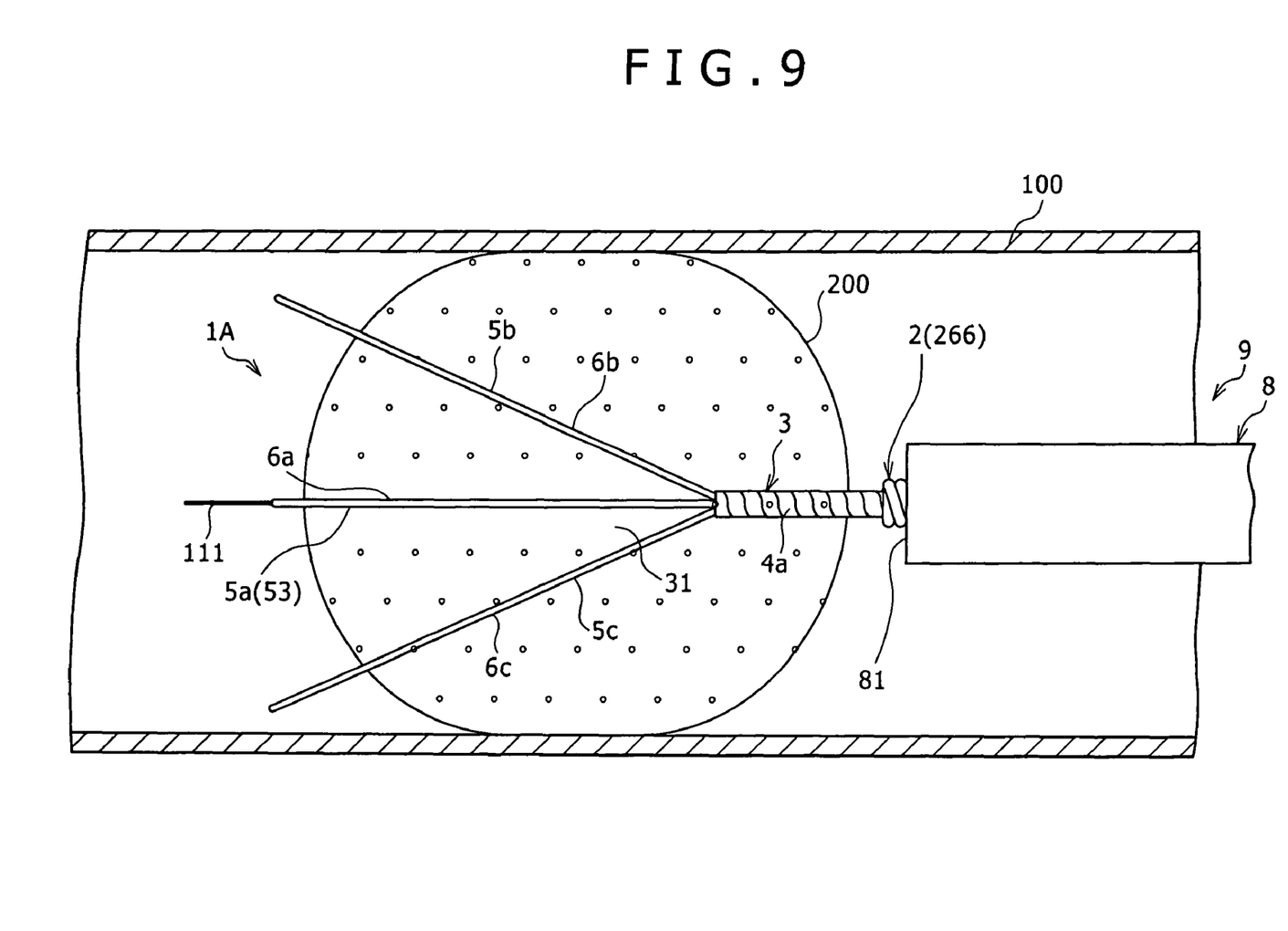
FIG. 9 is a general illustration of a manner of using the wire for removing an intravascular foreign body which is shown in FIG. 1.

[6] The wire 1A for removing an intravascular foreign body and the catheter 8 are then removed all together from the vessel, with the state shown in FIG. 9 (the tightened state) being maintained. Thus, the embolus 200 is captured in the guiding catheter or sheath introducer.

Figure 10:
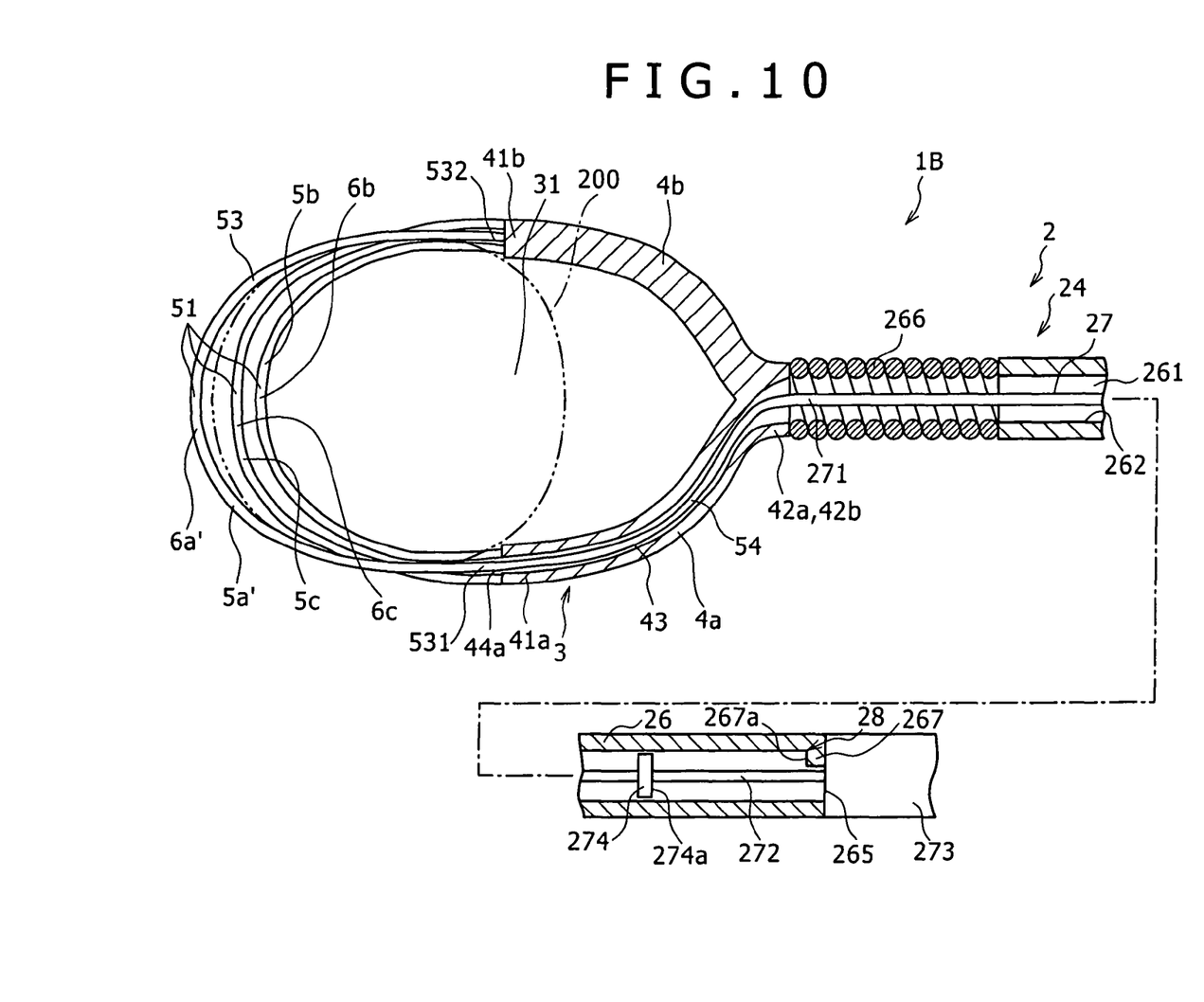
FIG. 10 is a plan view, partially in longitudinal cross-section, of a wire for removing an intravascular foreign body according to a second embodiment.
Figure 11:
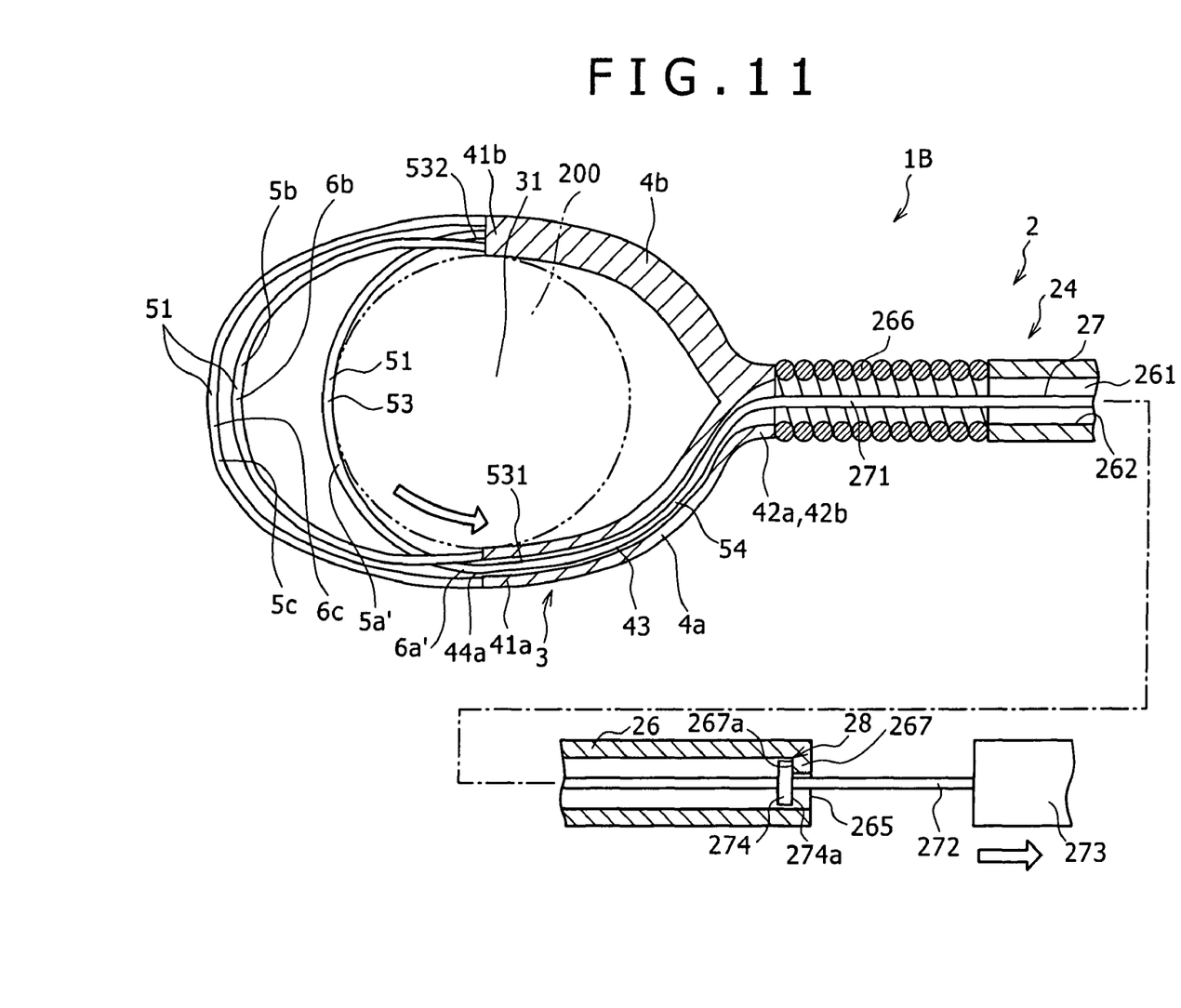
FIG. 11 is a plan view, partially in longitudinal cross-section, of the wire for removing an intravascular foreign body according to the second embodiment.

FIGS. 10 and 11 are plan views, partially in longitudinal cross-section, of a wire for removing an intravascular foreign body according to a second embodiment of the present invention. The following description will primarily describe features of the second embodiment differing from the first embodiment described above. Thus, a detailed description of features associated with the second embodiment of the wire for removing an intravascular foreign body which are the same as those associated with the first embodiment will not be repeated.

The wire for removing an intravascular foreign body according to the second embodiment is identical with that pertaining to the first embodiment, except for the construction of the branch wire and the filaments.

As shown in FIG. 10, the wire 1B for removing an intravascular foreign body according to the second embodiment utilizes two branch wires 4a, 4b, with one of the branch wires 4b being a solid wire.

The filament 5a' (the space forming part 53) has one end 532 fixed to the forward end 41b of the branch wire 4b. This fixation may be accomplished in any manner without specific restrictions. One way is to wind the end 532 of the filament 5a' around the forward end 41b of the branch wire 4b and bond them together by brazing, welding, or adhesion with an adhesive.

The other end 531 of the filament 5a' (the space forming part 53) is movably positioned in the branch wire 4a in the same way described above in connection with the first embodiment.

The wire 1B for removing an intravascular foreign body constructed as mentioned above permits the loop wire 6a' (comprised of the branch wires 4a, 4b and the filament 5a') to change in size as the manipulating member 273 is moved toward the base end direction. Because of this change in size, the loop wire 6a' moves from the first state illustrated in FIG. 10 representing its maximum size to the second state depicted in FIG. 11 representing its minimum size.

When the loop wire 6a' is in its first state, the embolus 200 is captured in the foreign body capturing space 31. As can be seen from a comparison of FIGS. 10 and 11, the captured embolus 200 is tightened by the loop wire 6a' when the loop wire 6a' assumes, or is moved to, its second state. In this way, it is possible to prevent the captured embolus 200 from slipping out of the foreign body capturing space 31 and hence to relatively reliably capture the embolus 200 and eventually to remove the embolus 200 from the vessel 100.

The filament 5a' can be provided with projections (11) and fine fibers (7) in a manner similar to that described above. If the filament 5a' is provided with the projections 11 and the fine fibers 7, the projections 11 and the fine fibers 7 turn (shift position relative to the capturing space 31) as the loop wire 6a' shrinks and is pulled (turns) in the direction of the arrow (counterclockwise direction) shown in FIG. 11. The turning of the projections 11 and the fine fiber 7 facilitate the rotation of the embolus 200 captured by the projections 11 and the fine fibers 7. If it is not desirable that the embolus 200 rotates, the filament 5a' should not be provided with the projections 11 and the fine fibers 7.

The other filaments 5b, 5c may also be provided with projection (11) and fine fibers (7) similar to those described above.

The space forming part 53 varies in the rate of reduction of its length depending on the particular embodiment. This is apparent from the structure of the loop wire 6a in the first embodiment and the structure of the loop wire 6a' in the second embodiment. For example, in the first embodiment, the loop wire 6a decreases in size (periphery) by 2 mm when the manipulating part 273 is moved 1 mm. On the other hand, in the second embodiment, the loop wire 6a' decreases in size by 1 mm when the manipulating part 273 is moved 1 mm.

The fact that the space forming part 53 varies in the rate of reduction of its length depending on which embodiment is used (wire 1A or 1B) advantageously allows selection of a particular configuration depending upon the results sought to be achieved. For example, if it is desirable to shrink or reduce the size of the loop wire more rapidly, it is preferable to use the wire 1A according to the first embodiment. On the other hand, if it is desirable to shrink or reduce the size of the loop wire more slowly, it is preferable to use the wire 1B according to the first embodiment.

Selection of the wires 1A and 1B should be made as follows. Where a subtle adjustment is necessary for the size of the loop wire, it is recommended to use the wire 1B, because the diameter of the forward end 271 is smaller than that of the wire 1A. This means that the loop wire can be made smaller with less friction during operation.

It is to be understood that the foregoing description of several embodiments of the wire for removing an intravascular foreign body and the medical instrument are not intended to restrict the scope of the present invention as the various features of the wire and medical instrument may be modified or replaced with (or reinforced with) features having a similar operation or function.

Two or more of the features in the above-mentioned embodiments may be combined to complete the wire for removing an intravascular foreign body. For example, the first embodiment may be modified such that the filaments at both sides of the central filament are constructed so that the length of the space forming part changes as in the case of the central filament. This modification permits the same wire to vary in the rate of reduction of the length of the space forming part differently for the central filament and the outside filaments. The effect of this modification is that the loop wire can be reduced in size in conformity with the shape of the embolus, thus further ensuring a relatively reliable capture of the foreign body. In this case, the embolus is tightened in three directions, so that it is possible to capture and hold the embolus more certainly.

The first embodiment may also be modified such that both ends of the space forming part are fixed to different linear bodies instead of being fixed to one linear body.

The number of the branch wires is not limited to two; and may include three or more branch wires.

Also, the number of filaments is not limited to three; and may include two, four or more filaments.

Further, the number of filaments for the space forming part which vary in length is not limited to one; and may include two or more such filaments.

The principles, preferred embodiments and manner of use of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A wire for removing an intravascular foreign body comprising:
    a flexible wire body possessing a central axis and a forward end;
    a branch part branching out from the forward end of the wire body;
    a plurality of filaments, each of the plurality of filaments extending across said branch part;
    the branch part and the filaments together forming a capturing space in which is to be captured a foreign body;
    the plurality of filaments comprising at least one first filament having opposite ends which are both axially movable relative to the branch part so that a loop formed by the at least one first filament and the branch part changes in size, the first filament lying entirely in a plane when the first filament is in a forward position for capturing the foreign body;
    the plurality of filaments also comprising at least one second filament having opposite ends which are both axially non-movable relative to the branch part;
    a movable body to which the ends of the at least one filament are connected so that with the foreign body positioned in the capturing space the movable body is movable to axially move the ends of the at least one first filament in a proximal direction relative to the branch part and relative to the at least one second filament to tighten the foreign body in the capturing space by engagement with the at least one first filament; and
    a continuation of the central axis of the wire body lying in said plane of the first filament.

2. The wire for removing an intravascular foreign body according to claim 1, wherein at least a part of the branch part is constructed of a hollow wire through which passes a part of the at least one first filament.

3. The wire for removing an intravascular foreign body according to claim 1, wherein the branch part comprises two branch wires each possessing a distal end, the two branch wires extend outwardly away from one another in a direction toward the distal ends of the branch wires, each of the ends of the at least one second filament being fixed to one of the branch wires.

4. The wire for removing an intravascular foreign body according to claim 1, wherein the plurality of filaments comprises a pair of second filaments which each have opposite ends which are both axially non-movable relative to the branch part.

5. The wire for removing an intravascular foreign body according to claim 1, further comprising means for controlling a minimum size of the loop.

6. The wire for removing an intravascular foreign body according to claim 1, wherein the at least one first filament is provided with a plurality of projections projecting into the capturing space.

7. The wire for removing an intravascular foreign body according to claim 1, wherein the at least one first filament is provided with a plurality of flexible fibers projecting into the capturing space.

8. The wire for removing an intravascular foreign body according to claim 1, wherein the at least one first filament is provided with a plurality of flexible fibers projecting into the capturing space and a plurality of projections projecting into the capturing space, the flexible fibers being more flexible than the projections.

9. A medical instrument comprising:
    the wire for removing an intravascular foreign body according to claim 1; and
    a catheter having a lumen adapted to receive the wire for removing an intravascular foreign body.

10. The wire for removing an intravascular foreign body according to claim 1 further comprising:
    a second branch part wherein the opposite ends of the at least one first filament are both movable relative to the branch parts and the opposite ends of the at least one second filament are both axially non-movable relative to the branch parts.

11. The wire for removing an intravascular foreign body according to claim 1, wherein the plurality of filaments comprises a third filament, the second and third filaments being inclined so that a distance from each of the second and third filaments to the central axis of the wire body increases in a direction away from the wire body.

12. The wire for removing an intravascular foreign body according to claim 1, wherein the plurality of filaments comprises a third filament having opposite ends, each of the ends of the third filament being fixed to the branch part in an axially non-movable manner so that each end of the third filament is axially non-movable relative to the respective branch wire.

13. The wire for removing an intravascular foreign body according to claim 12, wherein the second filament is positioned on one side of said plane while the third filament is positioned on an opposite side of said plane, the second and third filaments being inclined so that a distance from each of the second and third filaments to the plane increases in a direction away from the branch part.

14. The wire for removing an intravascular foreign body according to claim 1, wherein the branch part comprises two branch wires each possessing a distal end, the two branch wires extend away from one another in a direction toward the distal ends of the two branch wires, each of the ends of the at least one second filament being fixed to one of the branch wires, each branch wire comprising a hollow portion, a portion of the first filament being movably positioned in the hollow portion of each of the two branch wires.

15. The wire for removing an intravascular foreign body according to claim 14, wherein the plurality of filaments also comprises a third filament, the second filament being positioned on one side of the plane and the third filament being positioned on a side of the plane opposite the second filament.

16. A wire for removing an intravascular foreign body comprising:
    a flexible wire body possessing a forward end, the wire body having an outer dimension permitting the flexible wire to be positioned in a blood vessel of a living body;
    two branch wires connected to the forward end of the wire body and extending in a forward direction from the forward end of the flexible wire body;
    the two branch wires branching outwardly away from one another so that a distance between the two branch wires is greater farther away from the forward end of the wire body than nearer to the wire body;

each of the two branch wires having a forward end;
a plurality of filaments each of the plurality of filaments extending between the forward ends of the two branch wires;
the two branch wires and the filaments together forming a capturing space in which is to be captured a foreign body in the blood vessel, the two branch wires and filaments having outer dimensions permitting placement in the blood vessel of the living body;
the two branch wires and at least one of the filaments together forming a loop wire;
the at least one filament having opposite ends that are both axially movable relative to the two branch wires to change a peripheral length of the loop wire;
the two branch wires both being hollow, one of the ends of the at least one filament being movably positioned within one of the two hollow branch wires and the other end of the at least one filament being movably positioned within the other hollow branch wire; and
the plurality of filaments comprises a second filament having opposite ends that are both fixed to and axially non-movable relative to the two branch wires.

17. The wire for removing an intravascular foreign body according to claim 16, wherein the at least one filament is a first filament, and the plurality of filaments comprises a third filament, the first filament lying in a plane when the first filament is in a forward position for capturing the foreign body, the second filament being positioned on one side of the plane and the third filament being positioned on a side of the plane opposite the second filament.

18. The wire for removing an intravascular foreign body according to claim 17, wherein the flexible wire body possesses a central axis lying in the plane.

19. The wire for removing an intravascular foreign body according to claim 16, wherein the opposite ends of said at least one filament are connected to an elongated body movably positioned within the wire body and connected to a manipulating member which is operable to change the peripheral length of the loop wire.

20. The wire for removing an intravascular foreign body according to claim 16, wherein the plurality of filaments comprises a third filament, the second and third filaments being inclined so that a distance from each of the second and third filaments to a central axis of the wire body increases in a direction away from the wire body.

21. The wire for removing an intravascular foreign body according to claim 16, wherein the two branch wires are the only branch wires that are connected to the forward end of the flexible wire body and that extend in the forward direction from the forward end of the flexible wire body.

22. A wire for removing an intravascular foreign body comprising:
a flexible wire body possessing a central axis and a forward end, the wire body having an outer dimension permitting the flexible wire to be positioned in a blood vessel of a living body;
a plurality of loop wires connected to the flexible wire body, the loop wires possessing an outer dimension permitting the loop wires to be positioned in the blood vessel of the living body;
the loop wires together defining a capturing space in which is to be captured a foreign body in the blood vessel;
the first loop wire comprising a branch part connected to the forward end of the wire body and a first filament, the branch part comprising two branch wires branching away from one another, each branch wire having a forward end, the first filament extending between the forward ends of the two branch wires, the second loop wire comprising a second filament extending between the forward ends of the two branch wires;
the loop wires comprising at least a first loop wire having opposite ends which are both axially movable relative to the flexible wire body, the first loop wire lying entirely in a plane when the first loop wire is positioned in a forward position for capturing the foreign body;
the loop wires also comprising at least a second loop wire having opposite ends which are both axially non-movable relative to the flexible wire body;
means connected to the first loop wire for reducing an area enclosed by the first loop wire by moving the first loop wire in a proximal direction relative to the second loop wire so that the foreign body positioned in the capturing space is engaged by the first loop wire and held by the first loop wire; and
a continuation of the central axis of the wire body lying in said plane of the first loop wire.

23. The wire for removing an intravascular foreign body according to claim 22, wherein the second filament has two ends each fixed to one of the forward ends of the branch wires.

24. The wire for removing an intravascular foreign body according to claim 22, wherein the the first filament has opposite ends, the ends of the first filament being movably positioned within respective hollow portions of the branch part to move relative to the branch part, the means for reducing the area enclosed by the at least one loop wire comprising an elongated body movably positioned within the flexible wire body and a manipulating member connected to the elongated body and operable to move the elongated body, the first filament being connected to the elongated body to move together with the elongated body.

25. The wire for removing an intravascular foreign body according to claim 22, wherein the branch wires comprise first and second branch wires, each of the first and second branch wires having a hollow interior and extending in a forward direction from the forward end of the flexible wire body, the flexible wire body having a hollow interior communicating with the hollow interior of the first and second branch wires, the first and second branch wires diverging away from one another in the forward direction, one of the ends of the first filament being movably positioned in the hollow interior of the first branch wire, the other end of the first filament being movably positioned in the hollow interior of the second branch wire.

26. The wire for removing an intravascular foreign body according to claim 25, wherein the loop wires also comprise a third filament having opposite ends, one end of the second filament and one end of the third filament being fixed to the first branch wire in an axially non-movable manner, the other end of the second filament and the other end of the third filament being fixed to the second branch wire in an axially non-movable manner.

27. The wire for removing an intravascular foreign body according to claim 26, wherein the second filament is positioned on one side of the plane and the third filament is positioned on a side of the plane opposite the second filament.

28. A wire for removing an intravascular foreign body comprising:
a flexible wire body possessing a forward end, the flexible wire body possessing a hollow interior in which is movably positioned a movable body which is movable relative to the flexible wire body;
a branch part branching out from the forward end of the wire body;

a plurality of filaments each of the plurality of filaments extending across said branch part;

the branch part and the filaments together forming a capturing space in which is to be captured a foreign body;

the plurality of filaments comprising at least one first filament having opposite ends and at least one second filament having opposite ends;

the branch part comprises two hollow branch wires each possessing a distal end, the two branch wires extending outwardly away from one another in a direction toward the distal ends of the branch wires;

both of the hollow branch wires communicating with the hollow interior of the flexible wire body;

each of the ends of the first filament being movably positioned in a respective one of the two hollow branch wires so that a loop formed by the first filament and the two branch wires changes in size;

each of the ends of the second filament being fixed to a respective one of the two branch wires in an axially non-movable manner so that each end of the second filament is axially non-movable relative to the respective branch wire;

each end of the first filament comprising a connecting part that is connected to the movable body so that with the foreign body positioned in the capture space, the movable body is movable relative to the flexible wire body in a proximal direction away from the distal end of each branch wire to cause the ends of the first filament to move in the respective hollow branch wires relative to the ends of the second filament to reduce the size of the loop so that the first filament engages and tightens a hold on the foreign body in the capture space.

29. The wire for removing an intravascular foreign body according to claim 28, wherein the plurality of filaments comprises a third filament having opposite ends, each of the ends of the third filament being fixed to a respective one of the two branch wires in an axially non-movable manner so that each end of the third filament is axially non-movable relative to the respective branch wire.

30. The wire for removing an intravascular foreign body according to claim 29, wherein the first filament lies in a plane, and the second filament is positioned on one side of the plane while the third filament is positioned on an opposite side of the plane, the second and third filaments being inclined so that a distance from each of the second and third filaments to the plane increases in a direction away from the respective branch wire.

31. The wire for removing an intravascular foreign body according to claim 28, wherein the first filament lies entirely in a plane when the first filament is in a forward position for capturing the foreign body, and a continuation of a central axis of the wire body lies in the plane.

* * * * *